US008283152B2

(12) United States Patent
Kim et al.

(10) Patent No.: US 8,283,152 B2
(45) Date of Patent: Oct. 9, 2012

(54) MICROORGANISM PRODUCING O-ACETYL-HOMOSERINE AND THE METHOD OF PRODUCING O-ACETYL-HOMOSERINE USING THE MICROORGANISM

(75) Inventors: So Young Kim, Gwacheon-si (KR); Yong Uk Shin, Yongin-si (KR); In Kyung Heo, Seoul (KR); Hyun Ah Kim, Namwon-si (KR); Chang Il Seo, Incheon (KR); Ju Eun Kim, Seoul (KR); Sung Kwang Son, Seoul (KR); Sang Mok Lee, Seoul (KR); Sung Hoo Jhon, Seoul (KR); Han Jin Lee, Seoul (KR); Kwang Ho Na, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 5 days.

(21) Appl. No.: 12/550,121

(22) Filed: Aug. 28, 2009

(65) Prior Publication Data

US 2011/0053253 A1 Mar. 3, 2011

(51) Int. Cl.
*C12N 1/21* (2006.01)
*C12P 21/06* (2006.01)

(52) U.S. Cl. .................................. 435/252.33; 435/69.1

(58) Field of Classification Search ........................ None
See application file for complete search history.

(56) References Cited

U.S. PATENT DOCUMENTS 7,211,415 B2 5/2007 Rieping et al.
2009/0253186 A1 10/2009 Kim et al. ..................... 435/116

FOREIGN PATENT DOCUMENTS

| | | | |
|---|---|---|---|
| EP | 1 253 195 | | 10/2008 |
| EP | 2 108 693 | A2 | 10/2009 |
| WO | 2005/075625 | | 8/2005 |
| WO | WO 2006/082252 | A2 | 8/2006 |
| WO | 2006/138689 | A2 | 12/2006 |
| WO | 2007/012078 | | 1/2007 |
| WO | 2008/013432 | | 1/2008 |
| WO | 2008/033001 | A1 | 3/2008 |

OTHER PUBLICATIONS

Bourhy et al. (J Bacteriol. Jul. 1997, vol. 179, p. 4396-4398).*
Hwang et al. (J Bacteriol. Mar. 2002; 184(5):1277-86).*
Belfaiza et al., "Direct Sulfhydrylation for Methionine Biosynthesis in *Leptospira meyeri*," *Journal of Bacteriology*, 180 (2): 250-255, 1997.
Lockwood et al., "D-Methionine Attenuates Inner Hair Cell Loss in Carboplatin-Treated Chinchillas," *Audiology & Neurotology*, 5 (5): 263-266, 2000.
Mato et al., "S-Adenosylmethionine: a control switch that regulates liver function," *The FASEB Journal*, 16: 15-26, 2002.
Mischoulon et al., "Role of S-adenosyl-L-methionine in the treatment of depression: a review of the evidence," *The American Journal of Clinical Nutrition, 76*: 1158S-1161S, 2002.
Posfai et al., "Versatile insertion plasmids for targeted genome manipulations in bacteria: isolation, deletion, and rescue of the pathogenicity island LEE of the *Escherichia coli* O157:H7 genome," *Journal of Bacteriology*, 179 (13): 4426-4428, 1997.
Rambaldi et al., *S-adenosyl-L-methionine for alcoholic liver diseases (Review)*, Issue 2, The Cochrane Collaboration, John Wiley & Sons, Ltd., 2009, 1-47.
Soeken et al., "Safety and efficacy of S-adenosylmethionine (SAMe) for osteoarthritis," *The Journal of Family Practice, 51* (5): 425-430, 2002.
Soeken et al., "Review: S-adenosylmethionine treats osteoarthritis as effectively as nonsteroidal anti-inflammatory drugs with fewer adverse effects," *ACP Journal Club, 138* (1): 21, 2003.
White et al., "Genome Sequence of the Radioresistant Bacterium *Deinococcus radiodurans* R1," *Science, 286* (5444): 1571-1577, 1999.
Database UniProt, Accession No. P57714, "RecName: Full=Homoserine O-acetyltransferase; EC=2.3.1.31," dated Nov. 2, 2010, 2 pages, (XP-002611946).
Database UniProt, Accession No. A0QSZ0, "RecName: Full=Homoserine O-acetyltransferase; EC=2.3.1.31," dated Nov. 2, 2010, 2 pages, (XP-002611947).
Database UniProt, Accession No. Q9RVZ8, RecName: Full=Homoserine O-acetyltransferase; EC=2.3.1.31, dated Nov. 2, 2010, 2 pages, (XP-002611972).
Extended European Search Report, for European Application No. 10250455.2, dated Dec. 14, 2010, 8 pages.
Gomes et al., "Production of L-methionine by submerged fermentation: A review," *Enzyme and Microbial Technology 37*:3-18, 2005.
Fleischmann et al., "metX gene product [*Mycobacterium smegmatis* str. MC2 155]," YP 886028.1 <GENBANK>, URL: http://www.ncbi.nlm.nih.gov/protein/118469217, download date Apr. 3, 2012, 1 page.
White et al., "homoserine O-acetyltransferase [*Deinococcus radiodurans* R1]," NP 294596.1 <GENBANK>, URL: http://www.ncbi.nlm.nih.gov/protein/NP_294596.1, download date Apr. 3, 2012, 2 pages.
"MetX gene product [*Pseudomonas aeruginosa* PAO1]," NP 249081.1 <GENBANK>, URL: http://www.ncbi.nlm.nih.gov/protein/NP_249081.1, download date Apr. 3, 2012, 3 pages.

* cited by examiner

*Primary Examiner* — Padma Baskar
(74) *Attorney, Agent, or Firm* — SEED IP Law Group PLLC

(57) ABSTRACT

Disclosed is a strain of *Escherichia* sp., capable of producing O-acetyl homoserine in high yield, with the introduction and enhancement therein of the activity of: homoserine acetyl transferase, aspartokinase and homoserine dehydrogenase; and at least one enzyme selected from a group consisting of phosphoenolpyruvate carboxylase, aspartate aminotransferase and aspartate semi-aldehyde dehydrogenase. Also, a method of producing O-acetyl homoserine using the strain is provided.

10 Claims, 5 Drawing Sheets

MICROORGANISM PRODUCING O-ACETYL-HOMOSERINE AND THE METHOD OF PRODUCING O-ACETYL-HOMOSERINE USING THE MICROORGANISM

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_407_SEQUENCE_LISTING.txt. The text file is 26 KB, was created on Mar. 7, 2011, and is being submitted electronically via EFS-Web.

BACKGROUND OF THE INVENTION

1. Field of the Invention

The present invention relates to a strain of *Escherichia* sp. capable of producing O-acetyl homoserine in high yield. More particularly, the present invention relates to a strain of *Escherichia* sp. capable of producing O-acetyl homoserine in high yield, in which the activity of homoserine acetyl transferase, aspartokinase and homoserine dehydrogenase, in combination with at least one enzyme selected from a group consisting of phosphoenolpyruvate carboxylase, aspartate aminotransferase and aspartate semi-aldehyde dehydrogenase, are introduced and enhanced. Also, the present invention is concerned with a method of producing O-acetyl homoserine using the strain.

2. Description of the Related Art

Methionine, an essential amino acid for the body, finds a variety of applications in the food and medical industries, such as the use thereof as an additive in animal feed and foods and as a material for parenteral nutrient solutions and medicines. Methionine acts as a precursor for choline (lecithin) and creatine and is used as a material useful for the synthesis of cysteine and taurine. Together with cysteine, methionine is one of two sulfur-containing proteinogenic amino acids. S-Adenosyl methionine, derived from L-methionine, serves as a methyl donor in vivo and is involved in the synthesis of various neurotransmitters in the brain. Methionine and/or S-adenosyl-L-methionine (SAM) is also found to prevent lipid accumulation in the liver and arteries and to alleviate depression, inflammation, liver diseases and muscle pain (Jeon B R et al., *J Hepatol.,* 2001 March; 34(3): 395-401).

As summarized below, methionine and/or S-adenosyl-L-methionine has been thus far known to have the in vivo functions of:

1) suppressing lipid accumulation in arteries and in the liver, where lipid metabolism is mediated, and improving blood circulation in the brain, the heart and the kidneys (J Hepatol. Jeon B R et al., 2001 March; 34(3): 395-401).

2) promoting the digestion, detoxication and excretion of toxic substances and the excretion of heavy metals such as Pb.

3) acting as an antidepressant when methionine is administered in a daily dose of from 800 to 1,600 mg (Am J Clin Nutr. Mischoulon D. et al., 2002 November; 76(5): 1158S-61S)

4) improving liver functions against liver diseases (FASEB J. Mato J M., 2002 January; 16(1): 15-26), particularly, against alcohol-induced liver injury (Cochrane Database Syst Rev., Rambaldi A., 2001; (4): CD002235)

5) showing an anti-inflammatory effect on osteoarthritis and promoting the healing of joints (ACP J Club. Sander O., 2003 January-February; 138(1): 21, J Fam Pract., Soeken K L et al., 2002 May; 51(5): 425-30).

6) acting as an essential nutrient to hair formation and preventing brittle hair and depilation (Audiol Neurootol., Lockwood D S et al., 2000 September-October; 5(5): 263-266).

Methionine for use in animal feed, foods and medicines can be synthesized chemically or biologically.

In the chemical synthesis route, on the whole, methionine is produced through the hydrolysis of 5-(β-methylmercaptoethyl)-hydantoin. However, the synthesized methionine is disadvantageously present in a mixture of L- and D-forms which needs a difficult additional process to separate them from each other. In order to solve this problem, the present inventors developed a biological method for selectively synthesizing L-methionine, a chemical which a patent (WO 2008/103432) has already been applied for. The method, termed in brief "a two-step process", comprises the fermentative production of an L-methionine precursor and the enzymatic conversion of the L-methionine precursor to L-methionine. The methionine precursor preferably includes O-acetylhomoserine and O-succinyl homoserine. The two-step process is evaluated on terms of having overcome the problems from which the conventional methods suffer, such as sulfide toxicity, feedback regulation in methionine synthesis by methionine and SAMe, and degradation of intermediates by cystathionine gamma synthase, O-succinylhomoserine sulfhydrylase and O-acetylhomoserine sulfhydrylase. Also, compared to the conventional chemical synthesis method of producing DL-methionine, the two-step process has the advantage of being selective for L-methionine only, with the concomitant production of organic acids, such as succinic acid and acetic acid as useful by-products.

Found as an intermediate in the biosynthesis pathway of methionine, O-acetyl-homoserine is used as a precursor for the production of methionine (WO 2008/013432). O-acetyl-homoserine is synthesized from L-homoserine and acetyl-CoA with the aid of O-acetyl transferase as shown in the following formula:

L-Homoserine+Acetyl-CoA→O-Acetyl-Homoserine.

In the U.S. patent application Ser. No. 12/062,835 of the present assignee are disclosed a microorganism strain into which a thrA gene responsible for aspartate kinase and homoserine dehydrogenase activity and a *Deinococcus*-derived metX gene coding for homoserine acetyl transferase are introduced to improve the biosynthesis of L-homoserine and O-acetyl-homoserine, respectively, and a method for producing O-acetyl homoserine at high yield using the same.

In this context, the present inventors conceived that the enhancement of the other three enzymes responsible for the catalytic reactions in the homoserine biosynthesis pathway, that is, phosphoenolpyruvate carboxylase (ppc), aspartate aminotransferase (aspC) and aspartate semi-aldehyde dehydrogenase (asd), would increase a higher production yield of O-acetyl homoserine than would the method of U.S. Ser. No. 12/062,835.

Like the concomitant enhancement of a series of the enzymes involved in the conversion from phosphoenolpyruvate to O-acetylhomoserine according to the present invention, attempts have been made to increase L-amino acid productivity by simultaneously expressing the enzymes which play important roles in the biosynthesis pathways of aspartate-derived L-amino acids, such as L-lysine, L-threonine and L-methionine.

EP00900872 is directed to the effective production of L-lysine, featuring an increase in the activities of a series of enzymes involved in the lysine biosynthesis, including dihydropicolinate synthase (dapA), aspartokinase (lysC), dihydropicolinate reductase (dapB), diaminopimelate dehydrogenase (ddh), tetrahydropicolinate succinylase (dapD), succinyl diaminopimelate diacylase (lysE), aspartate semi-aldehyde dehydrogenase (asd), phosphoenolpyruvate carboxylase (ppc), in *E. coli*. Japanese Patent Nos. JP2006-520460 and JP2000-244921 describes the effective production of L-theronine in *E. coli* by increasing the activities of aspartate semi-aldehyde dehydrogenase (asd), phosphoenolpyruvate carboxylase (ppc), aspartokinase (thrA), homoserine dehydrogenase (thrA), homoserine kinase (thrB) and threonine synthase (thrC). Also, WO 2007/012078 discloses a recombinant strain of *Corynebacterium* capable of producing increased levels of L-methionine in which genes coding for aspartokinase (lysC), homoserine dehydrogenase (hom), homoserine acetyl transferase (metX), O-acetylhomoserine sulfhydrylase (metY), cystathionine gamma synthase (metB), cobalamin-dependent transmethylase (metH); cobalamin-independent methionine synthase (metE), methyltetrahydrofolate reductase (metF), and glucose 6-phosphate dehydrogenase (zwf) are increased in expression level while genes coding for methionine repressor protein (mcbR), homoserine kinase (hsk), S-adenosylmethionine synthetase (metK), and threonine dehydratase (livA) are decreased in expression level.

All of the patents are related to the effective production of aspartate-derived L-amino acids, that is, L-lysine, L-threonine and L-methionine, respectively, featuring the employment of gene combinations depending on the respective products.

In the present invention, a series of enzymes responsible for the catalytic steps from phosphoenolpyruvate to O-acetylhomoserine in the O-acetylhomoserine biosynthesis pathway are designed to be increased in expression level to produce O-acetylhomoserine in higher yield, which has been mentioned nowhere in previous documentation. Further, the enzyme combination employed in the present invention is different from that employed for the production of the aspartate-derived L-amino acid, such as L-lysine, L-threonine or L-methionine, as the final products are different.

Leading to the present invention, intensive and thorough research into the production of O-acetyl homoserine in maximal yield, conducted by the present inventors, resulted in the finding that the concomitant enhancement of the genes encoding aspartate kinase and homoserine dehydrogenase (thrA), and homoserine acetyl transferase (metX) plus a gene encoding at least one enzyme selected from among phosphoenolpyruvate carboxylase (ppc), aspartate aminotransferase (aspC), and aspartate semi-aldehyde dehydrogenase (asd) in the form of a genomic DNA and/or a plasmid in a microorganism strain could bring about a significant increase in the production of O-acetyl homoserine.

SUMMARY OF THE INVENTION

It is therefore an object of the present invention to provide a microorganism strain capable of producing O-acetyl homoserine in high yield, which is designed to fortify a series of genes responsible for the enzymes involved in the homoserine biosynthesis pathway from phosphoenolpyruvate to O-acetyl homoserine.

It is another object of the present invention to provide a method of producing O-acetyl homoserine in high yield, using the microorganism strain.

In accordance with an aspect of the present invention, there is provided a strain of *Escherichia* sp., capable of producing O-acetyl homoserine in high yield, with the introduction and enhancement therein of the activity of: (a) homoserine acetyl transferase, aspartokinase and homoserine dehydrogenase; and (b) at least one enzyme selected from a group consisting of phosphoenolpyruvate carboxylase, aspartate aminotransferase and aspartate semi-aldehyde dehydrogenase.

In accordance with another aspect of the present invention, there is provided a method of producing O-acetyl homoserine in a culture medium, comprising fermenting the strain in the culture medium.

In accordance with a further aspect of the present invention, there is provided a method of producing L-methionine and acetate, comprising: (a) fermentating the strain to produce O-acetyl homoserine; (b) separating the O-acetyl homoserine; and (c) converting the O-acetyl homoserine, together with methyl mercaptan, into L-methionine and acetate in the presence of an enzyme selected from a group consisting of cystathionine ganuna synthase, O-acetyl homoserine sulfhydrylase, and O-succinyl homoserine sulfhydrylase.

According to the present invention, therefore, O-acetyl homoserine can be produced in high yield by fermenting a strain of *Escherichia* sp. which anchors all of the six genes aspartate kinase and homoserine dehydrogenase (thrA), homoserine acetyl transferase (metX), phosphoenolpyruvate carboxylase (ppc), aspartate aminotransferase (aspC), and aspartate semi-aldehyde dehydrogenase (asd), responsible for the biosynthesis pathway from phosphoenolpyruvate to O-acetyl homoserine, in the form of chromosomal DNA or plasmid DNA. In addition, the O-acetyl-L-homoserine produced by the strain of the present invention can be converted, as disclosed in WO2008/013432, entitled "Microorganism producing L-methionine precursor and method of producing L-methionine and organic acid from the L-methionine precursor", issued to the present inventors, into L-methionine in high yield.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
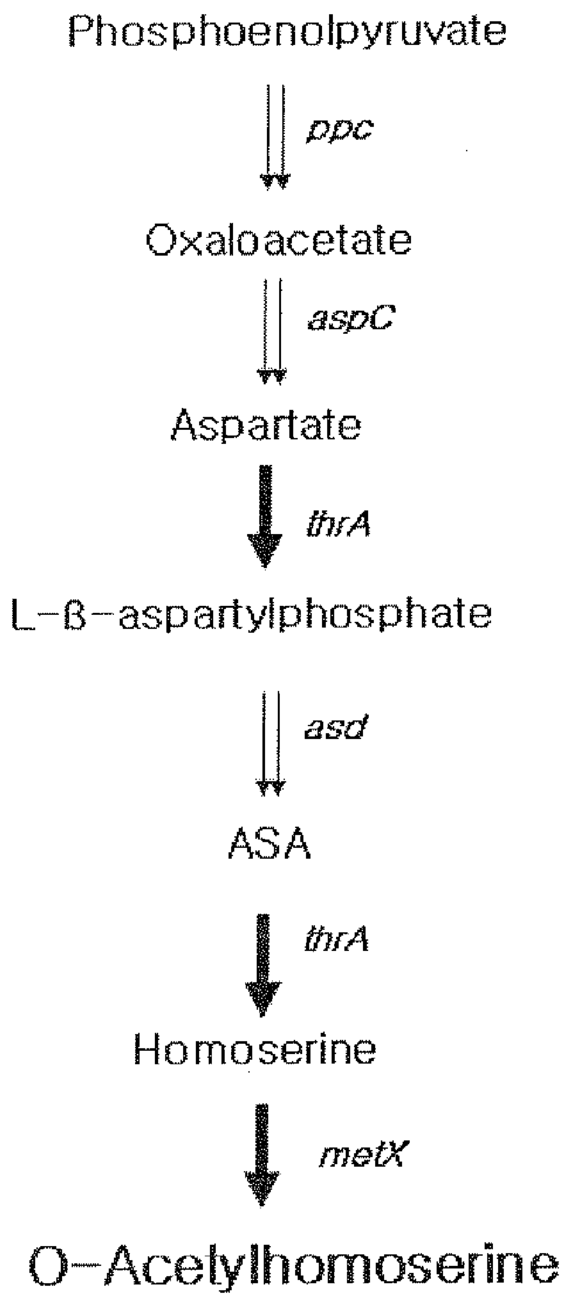
FIG. 1 is a schematic view showing an O-acetyl homoserine biosynthesis pathway of the strain according to the present invention.

In accordance with an aspect thereof, the present invention pertains to a strain of *Escherichia* sp. capable of producing O-acetyl homoserine in high yield, with the introduction and enhancement therein of the activity of (a) homoserine acetyl transferase, aspartokinase and homoserine dehydrogenase activities; and (b) at least one enzyme selected from a group consisting of phosphoenolpyruvate carboxylase, aspartate aminotransferase and aspartate semi-aldehyde dehydrogenase.

As used herein, the term "L-methionine precursor" is intended to refer to a metabolite found on the methionine biosynthesis pathway or a derivative thereof, and particularly to O-acetyl homoserine.

As used herein, the term "O-acetyl homoserine-producing strain" is intended to refer to a eukaryotic or prokaryotic microorganism which can produce O-acetyl homoserine intracellularly or extracellularly and particularly to a genetically modified microorganism which can accumulate O-acetyl homoserine therein. Examples of the strain useful in the present invention include *Escherichia* sp., *Erwinia* sp., *Serratia* sp., *Providencia* sp., *Corynebacteria* sp., *Pseudomonas* sp., *Leptospira* sp., *Salmonellar* sp., *Breuibacteria* sp., *Hypomononas* sp., *Chromobacterium* sp., *Norcardia* sp., fungi and yeasts, with preference for *Escherichia* sp., *Corynebacteria* sp. and *Leptospira* sp. and yeast. More preferred is *Escherichia* sp. Far more preferred is *Escherichia coli*. Further far more preferred is a strain of *E. coli* which can produce L-lysine, L-threonine, L-isoleucine or L-methionine. Most preferred is one derived from the strain of *E. coli* of Accession No. KCCM 10921P (deposited at Korean Culture Center of Microorganism, Yonsei University, Seodaemun-gu, Seoul 120-749, Republic of Korea, on Jan. 23, 2008) or KCCM 10925P deposited by the present assignee (deposited at Korean Culture Center of Microorganism, Yonsei University, Seodaemun-gu, Seoul 120-749, Republic of Korea, on Feb. 12, 2008; U.S. Ser. No. 12/062,835), or from FTR2533 (Accession No. KCCM 10541, deposited at Korean Culture Center of Microorganism, Yonsei University, Seodaemun-gu, Seoul 120-749, Republic of Korea on Dec. 9, 2003).

As used herein, the term "introduction and enhancement of activity" is intended to mean an increase in the intracellular activity of an enzyme encoded for by the corresponding gene, which can be generally achieved by the overexpression of the gene. There are many approaches to the overexpression of a target gene. For example, the overexpression may be implemented by the modification of a base in the promoter region and/or 5'-UTR for the target gene, by introducing the extra copy of the target gene on the chromosome, or by the introduction of the target gene in combination with an autologous or a heterologous promoter onto a vector, followed by the transformation of the vector into a microorganism strain. Further, a mutation in the ORF (open reading frame) of the target gene may result in the overexpression thereof. In numerical terms, when overexpression occurs, the corresponding protein increases in activity or concentration by 10%, 25%, 50%, 75%, 100%, 150%, 200%, 300%, 400%, or 500%, 1000% or up to 2000%, compared to when it is expressed in a natural state. Approaches to the introduction and enhancement of the activity of a gene include transformation with a plasmid carrying the corresponding gene, an increase in the number of gene copies, employment of a strong promoter for the gene, or a mutation in a preexisting promoter for the gene.

In a preferred embodiment thereof, the present invention provides a microorganism strain capable of producing O-acetyl homoserine in higher yield, with the introduction and enhancement of the activity of a series of six enzymes consisting of aspartate kinase and homoserine dehydrogenase (thrA), homoserine acetyl transferase (metX), phosphoenolpyruvate carboxylase (ppc), aspartate aminotransferase (aspC), and aspartate semi-aldehyde dehydrogenase (asd), and a method of producing O-acetyl homoserine using the same. Preferably, aspartate kinase and homoserine dehydrogenase (thrA) or homoserine acetyl transferase (metX) are introduced into and enhanced in cells by transformation with an expression vector carrying the corresponding genes while two or more copies of a gene coding for at least one selected from among phosphoenolpyruvate carboxylase (ppc), aspartate aminotransferase (aspC) and aspartate semi-aldehyde dehydrogenase (asd) may be located in the genome of the microorganism strain. Most preferably, all of these three genes are located in two or more copies in the genome of *E. coli*.

In greater detail, the microorganism strain is designed to increase the level of the metX gene coding for homoserine O-acetyltransferase responsible for the first step of the methionine bionsynthesis pathway, leading to an improvement in the synthesis of the L-methionine precursor O-acetyl homoserine. Herein, metX refers generally to a gene encoding a protein having the activity of homoserine O-acetyltransferase. For use in the present invention, new, exogenous homoserine O-acetyltransferase may originate from a variety of microorganisms. Examples of the microorganisms from which a gene coding for homoserine O-acetyltransferase can be obtained include *Corynebacterium* sp., *Leptospira Deinococcus* sp., *Pseudomonas* sp., or *Mycobacterium* sp., but are not limited thereto. Preferably, the homoserine O-acetyltransferase may be encoded by a gene originating from a strain selected from a group consisting of *Corynebacterium glutamicum, Leptospira meyeri, Deinococcus radiodurans, Pseudomonas aeruginosa* and *Mycobacterium smegmatis*. More preferably, the homoserine O-acetyltransferase has an amino acid sequence of UniProt Database Accession No. Q9RVZ8 (SEQ ID NO. 18), NP 249081 (SEQ ID NO. 19), or YP 886028 (SEQ ID NO. 20). The metX gene originating from *Leptospira meyeri* is known to show resistance to feedback inhibition (J Bacteriol. 1998 January; 180(2):250-5. Belfaiza J et al.). The other homoserine O-acetyltransferases were also found to be refractory to feedback inhibition in previous studies of the present inventors.

For example, the introduction and enhancement of homoserine O-acetyltransferase may be implemented by the introduction of metX or by the modification of a base in the 5'-UTR and/or promoter region for the target gene. Preferably, the target gene in combination with an autologous or a heterologous promoter is inserted into a vector, followed by the transformation of the vector into a microorganism strain. The introduction and enhancement of metX results in an increase in the synthesis of the methionine precursor.

In addition, the microorganism strain is designed to increase the activity of aspartokinase or homoserine dehydrogenase so as to improve the synthesis of the O-acetyl homoserine precursor homoserine. Herein, thrA refers generally to a gene encoding a peptide having the activity of aspartokinase and homoserine dehydrogenase. Preferably, the aspartokinase and homoserine dehydrogenase is encoded by a gene of Uniprot database Accession No: AP_000666. The thrA gene may be preferably introduced via a plasmid and remain as a plasmid DNA. That is, an expression vector carrying the thrA gene may be transformed into the strain. More preferably, both metX and thrA are introduced into the strain and remain as plasmid DNAs in the strain. That is, an expression vector carrying both metX and thrA is transformed into the strain.

In an embodiment of the present invention, the O-acetyl-L-homoserine-producing microorganism strain may be prepared as follows.

First, the microorganism strain is designed to accumulate O-acetyl-L-homoserine by increasing the number of copies of genes respectively encoding phosphoenolpyruvate carboxylase (ppc), aspartate aminotransferase (aspC) and aspartate semi-aldehyde dehydrogenase (asd). For this, these genes are cloned into respective pSG vectors useful for the integration of a gene into a chromosome, followed by transformation with the pSG vectors to increase the number of the respective genes to two or more copies. As a result, the expression of the genes is improved. Next, the genes coding for aspartate kinase and homoserine dehydrogenase (thrA) and homoserine acetyl transferase (metX) are introduced as plasmid DNAs into the microorganism strain. In this regards, a thrA-metX operon composed of a thrA gene (aspartate kinase and homoserine dehydrogenase), a metX gene (homoserine acetyl transferase) derived from *Deinococcus*, and a CJ1 promoter is constructed and cloned into pCL1920, a low copy plasmid, followed by the transformation of the recombinant plasmid into the strain which has 2 copies of each of the genes (phosphoenolpyruvate carboxylase (ppc), aspartate aminotransferase (aspC), and aspartate semi-aldehyde dehydrogenase (asd)). Therefore, the microorganism strain is improved in every step of the biosynthesis pathway from phsphoenolpyruvate to O-acetyl homoserine.

A series of the enzymes are responsible for the catalytic steps of the biosynthesis pathway from phosphoenolpyruvate to O-acetyl homoserine as shown in the following reaction formulas. Accordingly, the overexpression of the serial genes leads to the intracellular accumulation of O-acetyl homoserine.

Phosphoenolpyruvate+$H_2O$+$CO_2$<->Oxaloacetate+Phosphate

Oxaloacetate+Glutamate<->Aspartate+a-ketoglutarate

Aspartate+ATP<->Aspartyl-4-phosphate+ADP

Aspartyl-4-phosphate+NADPH<->Aspartate-semialdehyde+Phosphate+NADP+

Aspartate-semialdehyde+NADPH<->Homoserine

Homoserine+Acetyl-CoA<->O-Acetyl-homoserine+CoA

Genes coding respectively for phosphoenolpyruvate carboxylase, aspartate aminotransferase, aspartate semi-aldehyde dehydrogenase, aspartate kinase and homoserine dehydrogenase, and homoserine acetyl transferase are generally expressed as ppc, aspC, asd, thrA, and metX. These genes may be obtained from the genome sequences of *Escherichia coli* and *Deinococcus radiodurans* R1 disclosed previously (Mol Syst Biol. 2006; 2:2006.0007. Epub 2006 Feb. 21, Science. 1999 Nov. 19; 286(5444):1571-7). Also, the gene sequences may be obtained from public databases such as those constructed by the National Center for Biotechnology Information (NCBI) or the DNA Data Bank of Japan (DDBJ). For example, GenBank ID. No. 89110074 is given to ppc, GenBank ID. No. 85674274 to aspC, GenBank ID. No. 89110578 to asd, GenBank ID. No. 89106886 to thrA, and GenBank ID. No. 1799718 to metX. The microorganism strain thus prepared is improved in a series of catalytic steps extending from aspartate to O-acetyl homoserine on the biosynthesis pathway, thereby producing O-acetyl-L-homoserine in high yield. This O-acetyl homoserine-producing strain, CJM-XPA2 (pCJ-thrA(M)-metX-CL), named "*Escherichia coli* CA05-0567" was deposited at KCCM (Korean Culture of Microorganism, Eulim build, Hongje-1-Dong, Seodaemun-ku, Seoul, 361-221, Korea) on Aug. 11, 2009, with the accession No. KCCM11025P.

An L-methionine-producing strain may be prepared on the basis of an L-lysine-, an L-threonine-, or an L-isoleucine-producing strain, and preferably on the basis of an L-threonine-producing strain. In this case, these strains have already been adapted to synthesize homoserine and can be further engineered to produce the methionine precursor in a large amount by increasing the expression of metX.

As used herein, the term "L-threonine-producing strain" is intended to refer to a prokaryotic or eukaryotic microorganism which can produce L-threonine intracellularly. Examples of the strain useful in the present invention include *Escherichia* sp., *Erwinia* sp., *Serratia* sp., *Providencia* sp., *Corynebacteria* sp., *Pseudomonas* sp. or *Brevibacteria* sp., with preference for *Escherichia* sp. More preferred is *Escherichia coli.*

In a preferred embodiment of the present invention, the L-threonine-producing strain FRT2533 disclosed in WO 2005/075625 may be used. FTR2533 is derived from *Escherichia coli* TFR7624 which originates from the *Escherichia coli* Accession No. KCCM10236 which is in turn based on *Escherichia coli* TF4076. *Escherichia coli* Accession No. KCCM10236 expresses in high levels the ppc gene encoding an enzyme responsible for the formation of oxaloacetate from PEP, together with the genes encoding enzymes essential for the biosynthesis of threonine from aspartate, including thrA (aspartokinase, 1-homoserine dehydrogenase), thrB (homoserine kinase), and thrC (threonine synthase), thus showing increased productivity of L-threonine. *Escherichia coli* TFR7624 (KCCM10538) carries an inactivated tyrR gene which represses the expression of tyrB gene necessary for L-threonine biosynthesis. *Escherichia coli* FTR2533 (KCCM10541) is an L-threonine-producing *E. coli* strain carrying an inactivated galR gene.

In a preferred embodiment of the present invention, CJM2-X/pthrA(M)-CL (Accession No. KCCM 10925P), disclosed in U.S. Ser. No. 12/062,835, may be used. This strain is derived from *E. coli* FTR2533 by deleting metB, thrB, metJ and metA genes and inserting a *Deinococcus radiodurans*-derived metX gene at the metA locus, followed by transformation with an expression vector carrying a thrA gene.

Also, in a preferred embodiment of the present invention, CJM-X/pthrA(M)-CL (Accession No. KCCM 10921P), disclosed in U.S. Ser. No. 12/062,835, may be used. This strain is derived from *E. coli* CJM002 (Accession No. KCCM10568) by deleting metB, thrB, metJ and metA genes and inserting a *Deinococcus radiodurans*-derived metX gene at the metA locus, followed by transformation with an expression vector carrying a thrA gene.

Figure 2:
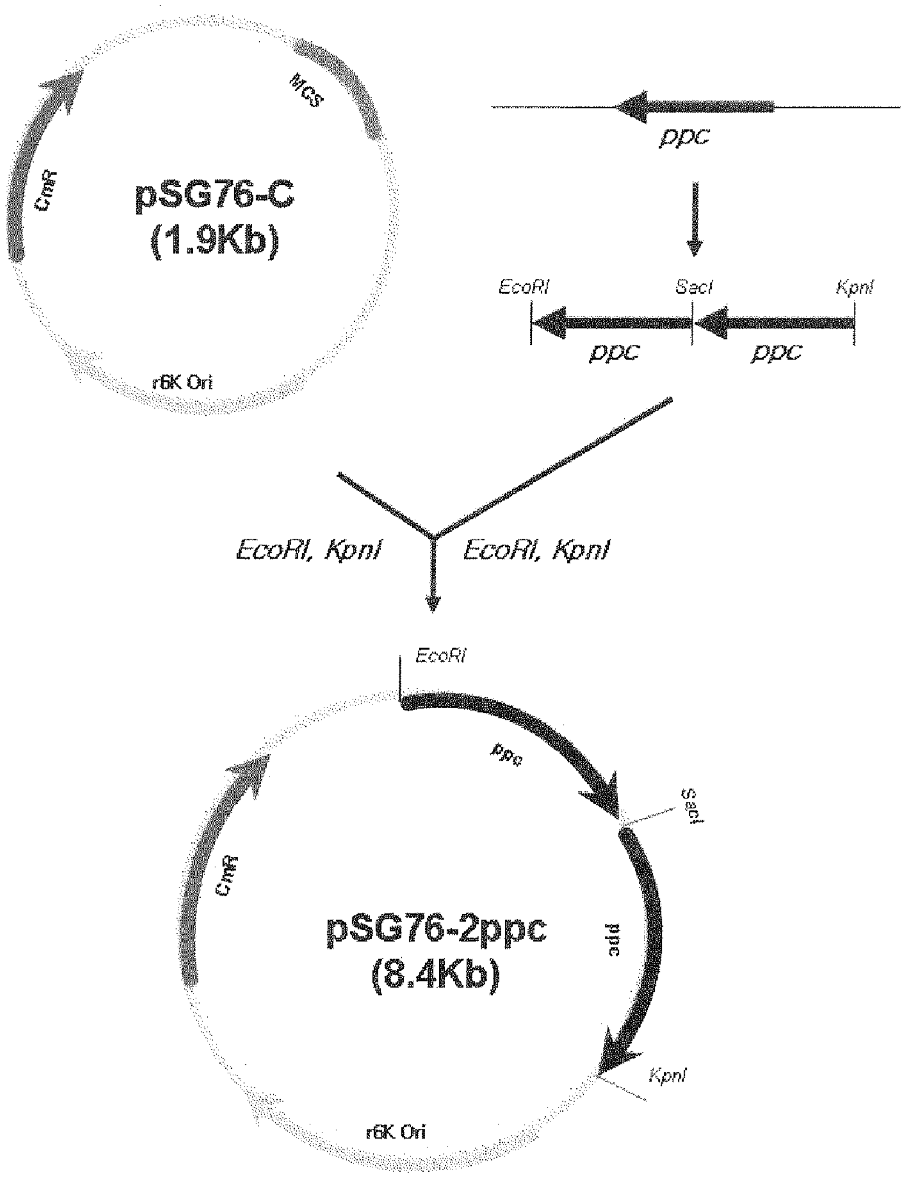
FIG. 2 is a schematic view showing the genetic map and construction of a pSG-2ppc vector for chromosomal integration.
Figure 4:
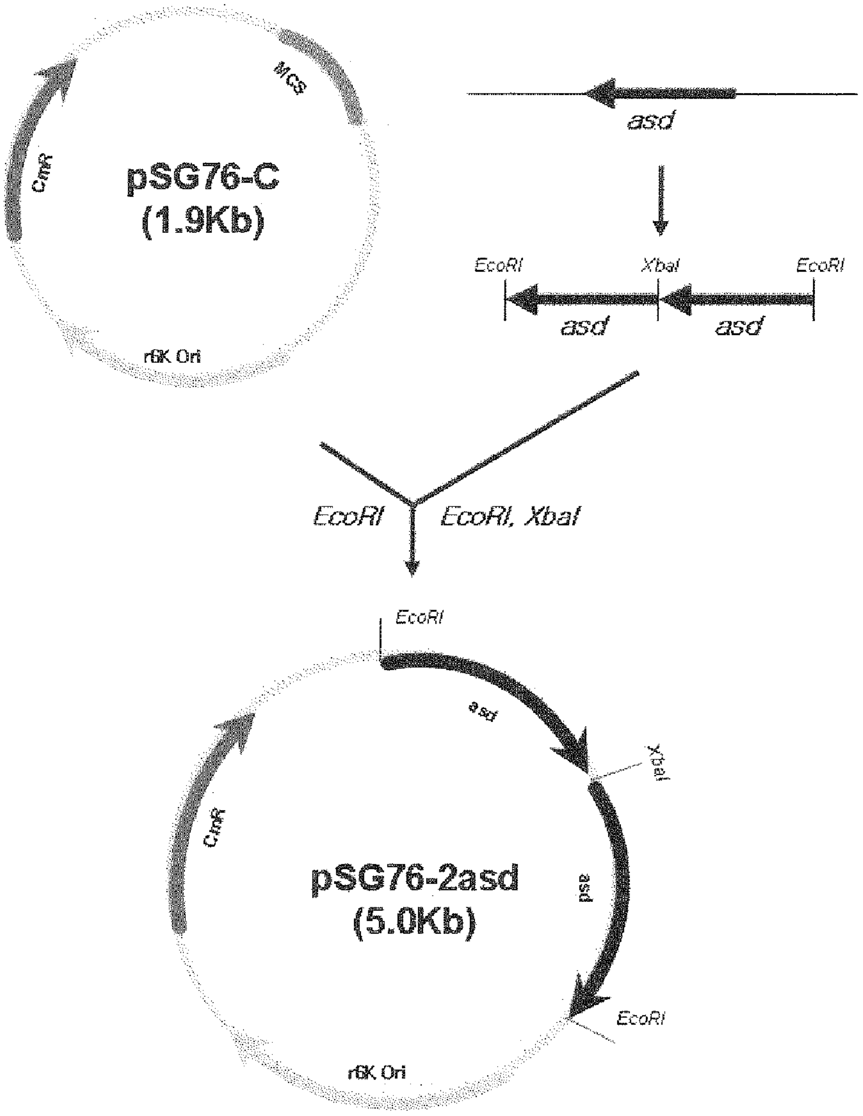
FIG. 4 is a schematic view showing the genetic map and construction of a pSG-2asd vector for chromosomal integration.
Figure 5:
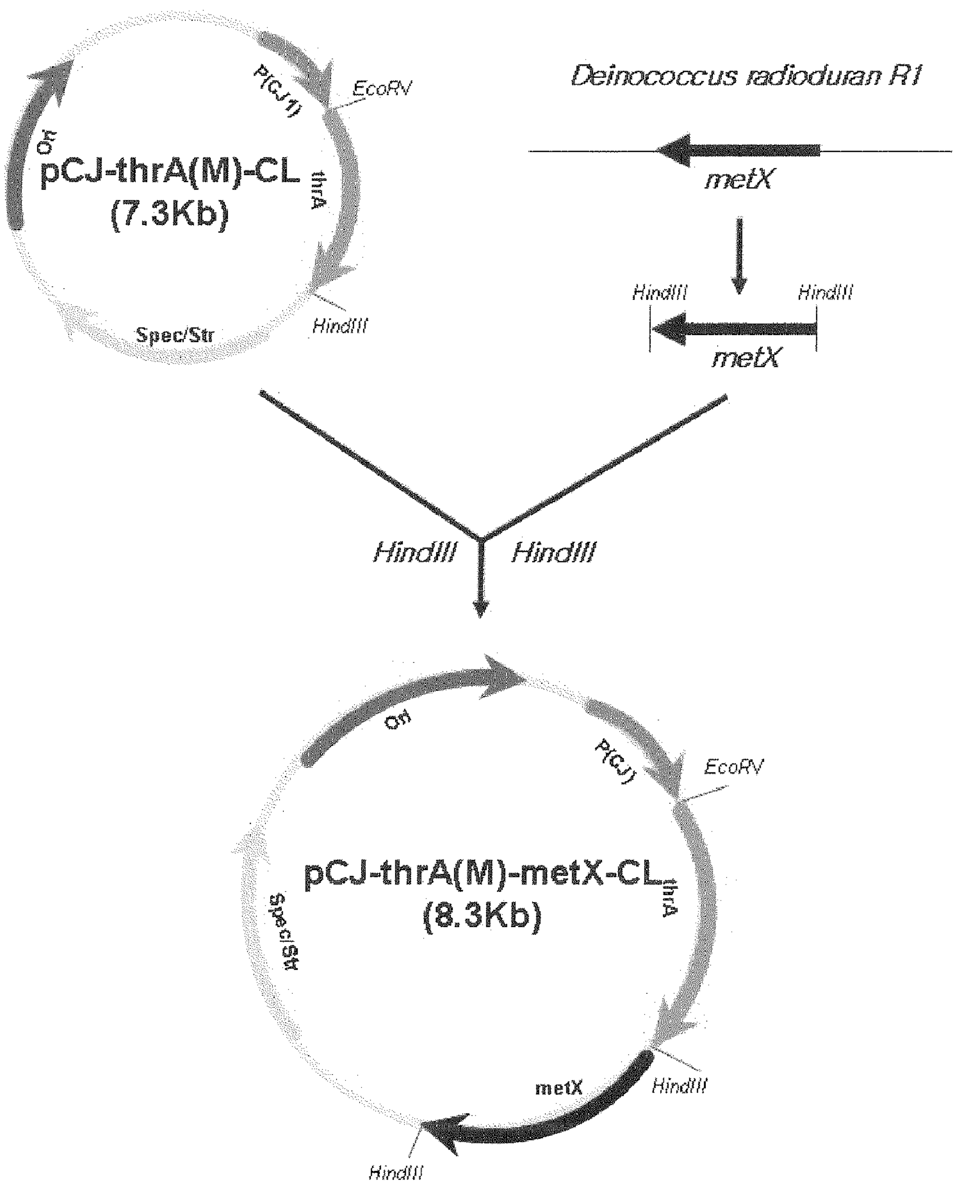
FIG. 5 is a schematic view showing the genetic map and construction of an expression vector pCJ-thrA(M)-metX-CL.

In concrete examples of the present invention, two copies of each of ppc, aspC and asd genes are integrated into the chromosome of *E. coli*. To this end, recombinant plasmids for the integration of respective genes are constructed, as shown in FIG. 2 for pSG-2ppc, FIG. 3 for pSG-2aspC, and FIG. 4 for pSG-2asd. Also, a recombinant expression vector pCJ-thrA(M)-metX-CL is constructed to express both thrA and metX simultaneously (FIG. 5). The recombinant vectors pSG-2ppc, pSG-2aspC and pSG-2asd are sequentially transformed into the CJM-X/pthrA(M)-CL strain enhanced with thrA and metX genes, disclosed in U.S. Ser. No. 12/062,835 (Accession No. KCCM 10921P). The transformed strain has two copies of each of the genes ppc, aspC, and asd integrated into the chromosome thereof and is named CJM-XPA2. Following transformed with the pCJ-thrA(M)-metX-CL vector, this mutant strain is cultured in flasks to quantitatively analyze the production of O-acetyl homoserine. Compared to the control CJM-X/pthrA(M)-CL (accession no. KCCM 10921P), the production yield of O-acetyl homoserine was found to increase by 3.6% from 29.1% to 32.7% in the strain having two copies of each of ppc, aspC, asd genes (responsible for the conversion of phosphoenolpyruvate to aspartate) integrated into the chromosome thereof, and by as high as 16.9% from 29.1% to 46% in the strain anchoring all of the genes ppc, aspC, asd, thrA and metX (responsible for the biosynthesis pathway from phosphoenolpyruvate to O-acetyl homoserine) in the form of chromosomal DNA or plasmid DNA. In consideration of the fact that the production yield of O-acetyl homoserine was 32.7% upon the enhancement of only the genes ppc, aspC and asd (responsible for the conversion of phosphoenolpyruvate to aspartate) and 37.5% upon the enhancement of only thrA and metX, when all of the genes responsible for the entire biosynthesis pathway extending from phosphoenolpyruvate to O-acetyl homoserine are enhanced together, the production yield of O-acetyl homoserine is further increased to 46% (Example 2, Table 2). Therefore, the strain prepared according to the present invention produces O-acetyl homoserine in greater yield than does the wild-type counterpart.

In accordance with another aspect thereof, the present invention is directed to a method of producing O-acetyl-homoserine, comprising the fermentation of the O-acetyl-homoserine producing *E. coli* strain in a culture medium to accumulate O-acetyl-homoserine in the medium.

In accordance with a further aspect thereof, the present invention is directed to a method of producing L-methionine and acetate, comprising (a) producing O-acetyl-homoserine through the fermentation of the O-acetyl homoserine-producing the strain of *Escherichia* sp. of the present invention; (b) separating the O-acetyl homoserine; and (c) converting the separated O-acetylhomoserine, together with methylmercaptan, into L-methionine and acetate in the presence of a transferase selected from among cystathionine gamma synthase, O-acetylhomoserine sulfhydrylase and O-succinylhomoserine sulfhydrylase.

When used in connection with the strain of the present invention, the method of producing L-methionine, which is based on the use of the converting enzyme, cystathionine gamma synthase, O-acetylhomoserine sulfhydrylase or O-succinylhomoserine sulfhydrylase as disclosed in WO 2008/013432, issued to the present inventors, can bring about a higher yield in L-methionine production.

The O-acetyl-L-homoserine-producing strain prepared above can be cultured in a medium and conditions known in the art. As is well understood by those familiar with the art, the culture method may be adjusted according to the strain used. The fermentation may be carried out in a batch, a continuous culture, or a fed-batch type, but is not limited thereto. A variety of fermentation methods are described in the following reference: "Biochemical Engineering" by James M. Lee, Prentice-Hall International Editions, pp 138-176.

The culture medium has to meet the culture conditions for a specific strain. A variety of microorganism culture mediums are described in the following reference: "Manual of Methods for General Bacteriology" by the American Society for Bacteriology, Washington D.C., USA, 1981. Generally, a culture medium includes various carbon sources, nitrogen sources and trace elements. Examples of the carbon source include carbohydrates such as glucose, sucrose, lactose, fructose, maltose, starch and cellulose; fats such as soybean oil, sunflower oil, castor oil and coconut oil; fatty acids such as palmitic acid, stearic acid, and linoleic acid; alcohols such as glycerol and ethanol; and organic acids such as acetic acid. These carbon sources may be used alone or in combination. Examples of the nitrogen source include organic nitrogen sources, such as peptone, yeast extract, gravy, malt extract, corn steep liquor (CSL) and bean flour, and inorganic nitrogen sources such as urea, ammonium sulfate, ammonium chloride, ammonium phosphate, ammonium carbonate and ammonium nitrate, which may be used alone or in combination. Additionally, the medium may contain potassium dihydrogen phosphate, dipotassium hydrogen phosphate and/or the corresponding sodium-containing salts thereof. Also, metal may be contained in the form of salts, like magnesium sulfate or iron sulfate, in the medium. In addition, amino acids, vitamins and proper precursors can be added as well. The mediums or the precursors can be added to the culture by batch-type or continuous type.

The pH of the culture can be adjusted with a suitable compound, for example, ammonium hydroxide, potassium hydroxide, ammonia, phosphate acid, and sulfuric acid. In order to inhibit the generation of bubbles in the culture, a defoaming agent such as fatty acid polyglycol ester may be used. To create aerobic conditions, the culture medium may be aerated with oxygen or oxygen-containing gas (e.g., air). The culture medium is maintained at 20~45° C. and preferably at 25~40° C. The strain is cultured to a desired level of the L-methionine precursor preferably for 10~160 hrs.

A better understanding of the present invention may be obtained through the following examples which are set forth to illustrate, but are not to be construed to limit the present invention.

EXAMPLE 1

Preparation of O-Acetyl Homoserine-Producing Strain

<1-1> Construction of pSG Vector for Chromosomal Integration of ppc

For use in the integration of ppc into the chromosome of *E. coli*, a pSG-2ppc vector was constructed.

The base sequence of the ppc gene was obtained from the GenBank database of the NIH (NCBI-gi: 89110074). On the basis of this base sequence, two sets of primers for the amplification of the ppc gene were synthesized: one set starting from 200 bp upstream of the start codon of the ppc ORF and containing the restriction enzyme sites EcoRI and Sad (SEQ ID NOS. 1 and 2); and the other set starting from 200 bp upstream of the start codon of the ppc ORF and containing the restriction enzyme sites Sad and KpnI (SEQ ID NOS. 3 and 4).

While the chromosomal DNA of *Escherichia coli* W3110 served as a template, PCR was performed using a set of primers of SEQ ID NOS. 1 and 2 or SEQ ID NOS. 3 and 4 in the presence of high-fidelity DNA polymerase PfuUltra™ (Stratagene), with 30 cycles of denaturation at 96° C. for 30 sec; annealing at 50° C. for 30 sec; and extension at 72° C. for 4 min.

The PCR products thus obtained were two kinds of about 3.1 kb ppc genes containing EcoRI and Sad sites, and Sad and KpnI sites therein, respectively.

After digestion with the restriction enzymes EcoRI and SacI, and SacI and KpnI, respectively, the two amplified ppc genes were ligated to each other and inserted into a pSG76-C vector treated with restriction enzymes EcoRI and KpnI (J Bacteriol. 1997 July; 179(13):4426-8), to construct a recombinant plasmid pSG-2ppc carrying two copies of the ppc gene. FIG. 2 shows the genetic map and construction of the vector pSG-2ppc for chromosomal integration of 2 copies of ppc.

<1-2> Construction of pSG Vector for Chromosomal Integration of aspC

For use in the integration of aspC into the chromosome of *E. coli*, a pSG-2aspC vector was constructed.

The base sequence of the aspC gene was obtained from the GenBank database of the NIH (NCBI-gi: 85674274). On the basis of this base sequence, a set of primers for the amplification of the aspC gene was designed to start from 200 bp upstream of the start codon of the aspC ORF and contain the restriction enzyme site BamHI (SEQ ID NOS. 5 and 6).

While the chromosomal DNA of *Escherichia coli* W3110 served as a template, PCR was performed using a set of primers of SEQ ID NOS. 5 and 6 in the presence of high-fidelity DNA polymerase PfuUltra™ (Stratagene), with 30 cycles of denaturation at 96° C. for 30 sec; annealing at 50° C. for 30 sec; and extension at 72° C. for 2 min.

The PCR product thus obtained was an about 1.5 kb aspC gene containing a BamHI site therein.

Figure 3:
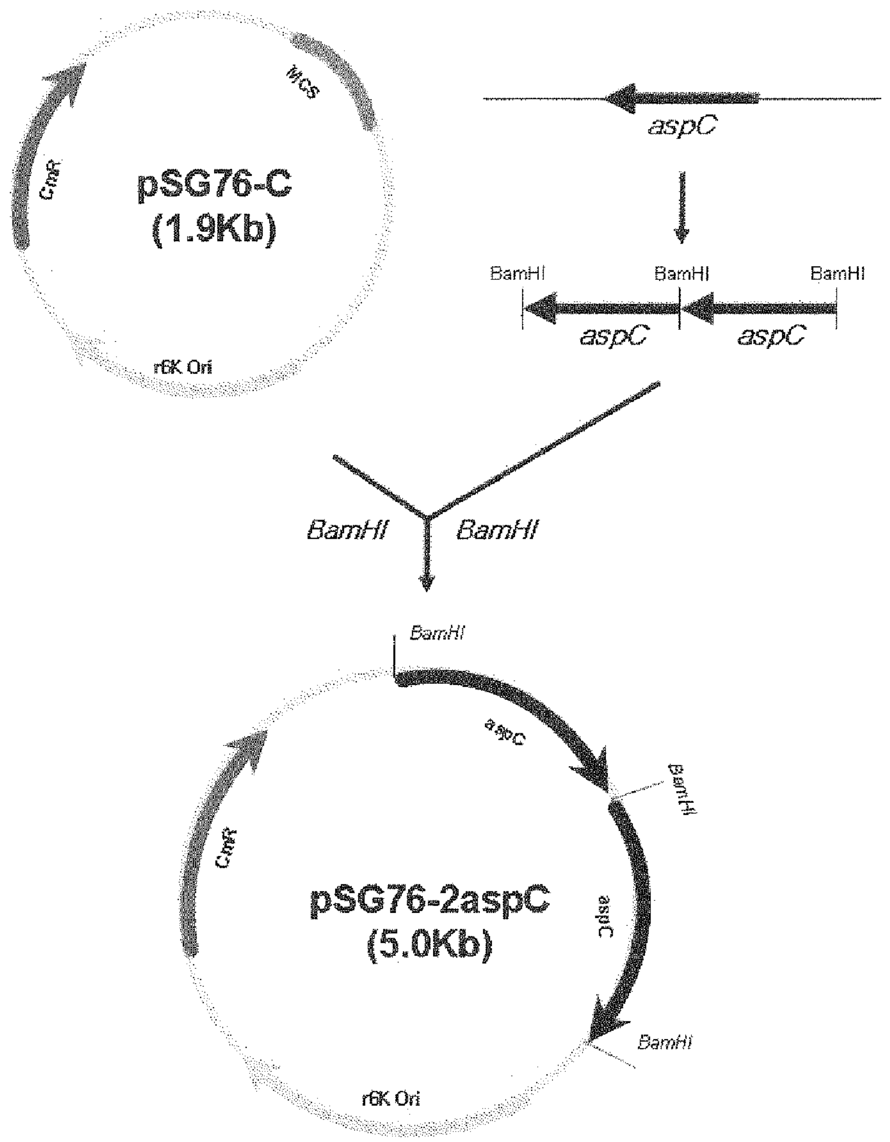
FIG. 3 is a schematic view showing the genetic map and construction of a pSG-2aspC vector for chromosomal integration.

After digestion with the restriction enzyme BamHI, the amplified apsC gene was ligated to a pSG76-C vector treated with the same restriction enzyme to construct a recombinant plasmid pSG-2aspC carrying two copies of the aspC gene. FIG. 3 shows the genetic map and construction of the vector pSG-2aspC for chromosomal integration of 2 copies of aspC.

<1-3> Construction of pSG Vector for Chromosomal Integration of asd

For use in the integration of asd into the chromosome of *E. coli*, a pSG-2asd vector was constructed.

The base sequence of the asd gene was obtained from the GenBank database of the NIH (NCBI-gi: 89110578). On the basis of this base sequence, two sets of primers for the amplification of the asd gene were synthesized: one set starting from 200 bp upstream of the start codon of the asd ORF and containing the restriction enzyme sites EcoRI and XbaI (SEQ ID NOS. 7 and 8); and the other set starting from 200 bp upstream of the start codon of the asd ORF and containing the restriction enzyme sites XbaI and EcoRI (SEQ ID NOS. 9 and 10).

While the chromosomal DNA of *Escherichia coli* W3110 served as a template, PCR was performed using a set of primers of SEQ ID NOS. 7 and 8 or SEQ ID NOS. 9 and 10 in the presence of high-fidelity DNA polymerase PfuUltra™ (Stratagene), with 30 cycles of denaturation at 96° C. for 30 sec; annealing at 50° C. for 30 sec; and extension at 72° C. for 2 min.

The PCR products thus obtained were two kinds of about 1.5 kb asd genes containing EcoRI and XbaI sites, and XbaI and EcoRI sites therein, respectively.

After digestion with the restriction enzymes EcoRI and XbaI, the amplified asd genes were ligated to each other and inserted into a pSG76-C vector treated with restriction enzyme EcoRI to construct a recombinant plasmid pSG-2asd carrying two copies of the asd gene. FIG. 4 shows the genetic map and construction of the vector pSG-2asd for chromosomal integration of 2 copies of asd.

<1-4> Construction of Recombinant pCJ-thrA(M)-metX-CL for Expression of ThrA and MetX For the biosynthesis of O-acetyl homoserine, thrA and metX were enhanced by introduction of a recombinant expression vector carrying the genes.

A nucleotide sequence of metX gene was obtained from NIH GenBank (NCBI gi: 1799718). On the basis of this nucleotide sequence, a set of primers was designed to cover a metX ORF ranging from ATG to TAA and have the restriction enzyme site HindIII at both ends thereof (SEQ ID NOS. 11 and 12).

Using the primers of SEQ ID NOS. 11 and 12, PCR was performed in the presence of high-fidelity DNA polymerase with 30 cycles of denaturation at 96° C. for 30 sec; annealing at 50° C. for 30 sec; and extension at 72° C. for 2 min during which the chromosomal DNA of *Deinococcus radioduran* R1 served as a template.

The PCR product thus obtained was an about 1 kb metX gene containing the restriction enzyme site HindIII.

After digestion with the restriction enzyme HindIII, the amplified metX gene was ligated to the thrA expression vector pCJ-thrA(M)-CL plasmid, disclosed in U.S. Ser. No. 12/062,835, which was previously treated with the same restriction enzyme, so as to construct a recombinant expression vector carrying both thrA and metX, termed pCJ-thrA(M)-metX-CL (FIG. 5).

<1-5> Preparation of O-Acetyl-Homoserine-Producing Strain

The plasmid pSG-2ppc carrying two copies of ppc gene, constructed in Example <1-1>, was transformed into the strain disclosed in U.S. Ser. No. 12/062,835, CJM-X/pthrA(M)-CL (Accession No. KCCM 10921P), followed by incubation on LB-Cm plates (Yeast extract 10 g/L, NaCl 5 g/L, Tryptone 10 g/L, chloramphenicol 25 μg/L) to select 10 chloramphenicol-resistant colonies for each transformant. The selected transformant anchored the pSG-2ppc vector at the chromosomal ppc site thereof. Then, the strain with two copies of ppc gene inserted thereinto was transformed with pAScep, an expression vector carrying the restriction enzyme I-SceI, so as to cleave the I-SceI site present in the pSG vector, followed by selection on LB-Ap (Yeast extract 10 g/L, NaCl 5 g/L, Tryptone 10 g/L, Ampicillin 100 μg/L). As a result, selected was a strain in which 2 copies of ppc gene were anchored at the chromosome thereof, with the pSG76-C vector removed therefrom. The same procedure as in the pSG-2ppc plasmid was repeated for pSG76C-2aspC and pSG76C-2asd vectors, constructed in Examples <1-2> and <1-3>, respectively, in order. Finally, a strain was derived from CJM-X/pthrA(M)-CL (Accession No. 10921P) with two copies of each of ppc, asd, and aspC inserted into the chromosome thereof, and was named CJM-XPA2.

Further, the CJM-XPA2 strain was transformed with the pCJ-thrA(M)-metX-CL vector constructed in Example <1-4> and then cultured on LB-Sp (Yeast extract 10 g/L, NaCl 5 g/L, Tryptone 10 g/L, Spectinomycin 25 μg/L) to select 10 colonies resistant to spectinomycin. The CJM-XPA2 (pCJ-thrA(M)-metX-CL), named "*Escherichia coli* CA05-0567" was deposited at KCCM (Korean Culture of Microorganism, Eulim build, Hongje-1-Dong, Seodaemun-ku, Seoul, 361-221, Korea) on Aug. 11, 2009, with the accession No. KCCM11025P. They were compared to each other for O-acetyl homoserine productivity.

EXAMPLE 2

Fermentation for O-Acetyl Homoserine Production

In order to examine the strains prepared in Example 1 for ability to produce the methionine precursor O-acetyl homoserine, they were cultured in Erlenmeyer flasks.

For this culture, the O-acetyl-homoserine titer medium shown in Table 1 was employed.

TABLE 1

| Composition of Medium for O-Acetyl-Homoserine Production | |
|---|---|
| Composition | Concentration(per liter) |
| Glucose | 60 g |
| Ammonium Sulfate | 17 g |
| $KH_2PO_4$ | 1.0 g |
| $MgSO_4 \cdot 7H_2O$ | 0.5 g |
| $FeSO_4 \cdot 7H_2O$ | 5 mg |
| $MnSO_4 \cdot 8H_2O$ | 5 mg |
| $ZnSO_4$ | 5 mg |
| $CaCO_3$ | 30 g |
| Yeast Extract | 2 g |
| Methionine | 0.15 g |
| Threonine | 0.15 g |

Single colonies which were generated on LB plates during incubation overnight at 32° C. were taken with platinum loops and inoculated respectively into 25 mL of the O-acetyl homoserine titer medium, followed by culturing at 32° C. for 42~64 hrs with shaking at 250 rpm. Each culture was quantitatively analyzed for O-acetyl homoserine using HPLC. The analysis data are summarized in Table 2, below.

Compared to the control CJM-X/pthrA(M)-CL (accession no. KCCM 10921P), as shown in Table 2, the production yield of O-acetyl homoserine was found to increase by 3.6% from 29.1% to 32.7% in the strain having two copies of each of ppc, aspC, asd genes, responsible for the conversion of phosphoenolpyruvate to aspartate, integrated into the chromosome thereof, and by as high as 16.9% from 29.1% to 46% in the strain anchoring all of the genes ppc, aspC, asd, thrA and metX, responsible for the biosynthesis pathway from phosphoenolpyruvate to O-acetyl homoserine, in the form of chromosomal DNA or plasmid DNA.

Taken together, the data obtained in the flask tests indicate that, in consideration of the fact that the production yield of O-acetyl homoserine is 32.7% upon the enhancement of only the genes ppc, aspC and asd, responsible for the conversion of phosphoenolpyruvate to aspartate, and 37.5% upon the enhancement of only thrA and metX, when all of the genes responsible for the entire biosynthesis pathway extending from phosphoenolpyruvate to O-acetyl homoserine are enhanced together, the production yield of O-acetyl homoserine is further increased to 46%. Therefore, the strain prepared according to the present invention produced O-acetyl homoserine in greater yield than does the wild-type counterpart.

TABLE 2

Flask Tests for O-Acetyl-Homoserine Production

| Strain | Plasmid | OAH production (g/L) | Yield (%) |
|---|---|---|---|
| CJM-X/pthrA(M)-CL | — | 17.5 | 29.1 |
| (Accession No. KCCM 10921P) | pCJ-thrA(M)-metX-CL | 22.5 | 37.5 |
| CJM-XPA2 | — | 19.6 | 32.7 |
| | pCJ-thrA(M)-metX-CL | 27.6 | 46.0 |

INDUSTRIAL APPLICABILITY

As described hitherto, the present invention provides a strain of *Escherichia* sp. which produces O-acetyl homoserine in high yield in a culture medium when fermented in the medium. In addition, the O-acetyl homoserine can be converted, along with methyl mercaptan, by the two-step process into L-methionine, with the concomitant production of acetic acid.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A strain of *Escherichia coli*, capable of producing O-acetyl homoserine in high yield, which overexpresses homoserine acetyl transferase, aspartokinase, homoserine dehydrogenase, phosphoenolpyruvate carboxylase, aspartate aminotransferase, and aspartate semi-aldehyde dehydrogenase, wherein aspartokinase and homoserine dehydrogenase, phosphoenolpyruvate carboxylase, aspartate aminotransferase, aspartate semi-aldehyde dehydrogenase, and homoserine acetyl transferase are encoded by respective genes thrA, ppc, aspC and asd from *Escherichia coli* and metX from *Deinococcus radiodurans.*

2. The strain as defined in claim 1, wherein the overexpression of the activity is achieved by transformation with a plasmid carrying a corresponding gene, by increasing a number of copies of a corresponding gene, or by an employment of a strong promoter for a corresponding gene.

3. The strain as defined in claim 2, wherein the overexpression of homoserine acetyl transferase, aspartokinase and homoserine dehydrogenase is achieved by introducing a plasmid carrying metX and thrA genes.

4. The strain as defined in claim 1, wherein the homoserine acetyl transferase has an amino acid sequence of SEQ ID NO:18, 19, or 20.

5. The strain as defined in claim 1, wherein the homoserine acetyl transferase has an amino acid sequence from *Deinococcus radiodurans* Q9RVZ8.

6. The strain as defined in claim 1, being from a strain capable of producing L-threonine, L-isoleucine or L-lysine.

7. The strain as defined in claim 1, being from *E. coli* CJM-X/pthrA (M)-CL, Accession No. KCCM 10921P.

8. The strain as defined in claim 1, being from *E. coli* CJM2-X/pthrA(M)-CL, Accession No. KCCM 10925P.

9. The strain as defined in claim 1, being from *E. coli* FTR2533, Accession No. KCCM 10541.

10. The strain as defined in claim 1, being deposited with Accession No. KCCM 11025P.

* * * * *

SEQUENCE LISTING

```
<160> NUMBER OF SEQ ID NOS: 20

<210> SEQ ID NO 1
<211> LENGTH: 31
<212> TYPE: DNA
<213> ORGANISM: Artificial Sequence
<220> FEATURE:
<223> OTHER INFORMATION: Forward primer for ppc

<400> SEQUENCE: 1

gccggaattc tgtcggatgc gatacttgcg c                                    31


<210> SEQ ID NO 2
<211> LENGTH: 30
<212> TYPE: DNA
<213> ORGANISM: Artificial Sequence
<220> FEATURE:
<223> OTHER INFORMATION: Reverse primer for ppc

<400> SEQUENCE: 2

gaaggagctc agaaaaccct cgcgcaaaag                                      30


<210> SEQ ID NO 3
<211> LENGTH: 31
<212> TYPE: DNA
```

-continued

<213> ORGANISM: Artificial Sequence
<220> FEATURE:
<223> OTHER INFORMATION: Forward primer for ppc

<400> SEQUENCE: 3
gccggagctc tgtcggatgc gatacttgcg c 31

<210> SEQ ID NO 4
<211> LENGTH: 30
<212> TYPE: DNA
<213> ORGANISM: Artificial Sequence
<220> FEATURE:
<223> OTHER INFORMATION: Reverse primer for ppc

<400> SEQUENCE: 4
gaagggtacc agaaaaccct cgcgcaaaag 30

<210> SEQ ID NO 5
<211> LENGTH: 30
<212> TYPE: DNA
<213> ORGANISM: Artificial Sequence
<220> FEATURE:
<223> OTHER INFORMATION: Forward primer for aspC

<400> SEQUENCE: 5
tccgagctca taagcgtagc gcatcaggca 30

<210> SEQ ID NO 6
<211> LENGTH: 30
<212> TYPE: DNA
<213> ORGANISM: Artificial Sequence
<220> FEATURE:
<223> OTHER INFORMATION: Reverse primer for aspC

<400> SEQUENCE: 6
tccgagctcg tccacctatg ttgactacat 30

<210> SEQ ID NO 7
<211> LENGTH: 27
<212> TYPE: DNA
<213> ORGANISM: Artificial Sequence
<220> FEATURE:
<223> OTHER INFORMATION: Forward primer for asd

<400> SEQUENCE: 7
ccggaattcc caggagagca ataagca 27

<210> SEQ ID NO 8
<211> LENGTH: 28
<212> TYPE: DNA
<213> ORGANISM: Artificial Sequence
<220> FEATURE:
<223> OTHER INFORMATION: Reverse primer for asd

<400> SEQUENCE: 8
ctagtctaga tgctctattt aactcccg 28

<210> SEQ ID NO 9
<211> LENGTH: 28
<212> TYPE: DNA
<213> ORGANISM: Artificial Sequence
<220> FEATURE:
<223> OTHER INFORMATION: Forward primer for asd

<400> SEQUENCE: 9
ctagtctaga ccaggagagc aataagca 28

<210> SEQ ID NO 10
<211> LENGTH: 27
<212> TYPE: DNA
<213> ORGANISM: Artificial Sequence
<220> FEATURE:
<223> OTHER INFORMATION: Reverse primer for asd

<400> SEQUENCE: 10
ccggaattct gctctattta actcccg 27

<210> SEQ ID NO 11
<211> LENGTH: 30
<212> TYPE: DNA
<213> ORGANISM: Artificial Sequence
<220> FEATURE:
<223> OTHER INFORMATION: Forward primer for metX

<400> SEQUENCE: 11
ctgaaagctt atgaccgccg tgctcgcggg 30

<210> SEQ ID NO 12
<211> LENGTH: 30
<212> TYPE: DNA
<213> ORGANISM: Artificial Sequence
<220> FEATURE:
<223> OTHER INFORMATION: Reverse primer for metX

<400> SEQUENCE: 12
cgccaagctt tcaactcctg agaaacgccc 30

<210> SEQ ID NO 13
<211> LENGTH: 1005
<212> TYPE: DNA
<213> ORGANISM: Deinococcus radioduran R1

<400> SEQUENCE: 13
atgaccgccg tgctcgcggg ccacgcctct gccctgctgc tgaccgaaga acccgactgt 60
tcggggccgc agacggtcgt tctcttccgg cgtgagccgc tgctgctcga ctgcggacgg 120
gcgctgagcg acgtgcgggt ggcctttcac acctacggca cgccgcgcgc cgacgccacg 180
ctggtgctgc acgccctgac cggcgacagc gcggtgcacg agtggtggcc cgactttctg 240
ggcgcgggcc ggccactgga cccggcagac gactacgtgg tgtgcgccaa cgtcctcggc 300
gggtgcgccg gcacgacgag cgccgctgaa ctcgccgcca cctgttccgg accggtgccg 360
ctcagcctgc gcgacatggc ccgggtgggg cgcgccctgc tggattctct cggcgtgcga 420
cgggtgcggg tcatcggcgc gagcatgggc gggatgctcg cctacgcctg gctgctggag 480
tgccccgacc tggtggaaaa ggccgtgatt ataggagccc cggcgcggca ctcgccctgg 540
gctattggac tgaacacggc ggcccgcagc gccattgccc tcgctcccgg cggcgagggg 600
ctgaaggtgg cgcgccagat tgccatgctc agttaccgca gccccgaaag cctaagccgc 660
acgcaggcgg ggcagcgcgt gccgggggtg cccgccgtta cgtcttacct gcactaccaa 720
ggcgaaaaac tcgccgcccg cttcgacgag cagacctact gcgccctcac ctgggcgatg 780
gacgcctttc agccgagcag cgccgacctc aaagcggtgc gcgcgccggt actcgtcgtc 840
ggcatctcca gcgatctgct ctaccccgcc gccgaggtcc gcgcctgcgc cgccgagctt 900
ccccacgccg actactggga actgggcagc attcacggcc acgacgcctt tttgatggac 960
ccacaggact tgccggagcg ggtgggggcg tttctcagga gttga 1005

<210> SEQ ID NO 14

-continued

<211> LENGTH: 3125
<212> TYPE: DNA
<213> ORGANISM: Escherichia coli W3110

<400> SEQUENCE: 14
gccgcaataa tgtcggatgc gatacttgcg catcttatcc gaccgacagt gactcaaacg 60
atgcccaact gtaggccgga taaggcgctc gcgccgcatc cggcactgtt gccaaactcc 120
agtgccgcaa taatgtcgga tgcgatactt gcgcatctta tccgacctac acctttggtg 180
ttacttgggg cgatttttta acatttccat aagttacgct tatttaaagc gtcgtgaatt 240
taatgacgta aattcctgct atttattcgt ttgctgaagc gatttcgcag catttgacgt 300
caccgctttt acgtggcttt ataaaagacg acgaaaagca aagcccgagc atattcgcgc 360
caatgcgacg tgaaggatac agggctatca aacgataaga tggggtgtct ggggtaatat 420
gaacgaacaa tattccgcat tgcgtagtaa tgtcagtatg ctcggcaaag tgctgggaga 480
aaccatcaag gatgcgttgg gagaacacat tcttgaacgc gtagaaacta tccgtaagtt 540
gtcgaaatct tcacgcgctg gcaatgatgc taaccgccag gagttgctca ccaccttaca 600
aaatttgtcg aacgacgagc tgctgcccgt tgcgcgtgcg tttagtcagt tcctgaacct 660
ggccaacacc gccgagcaat accacagcat ttcgccgaaa ggcgaagctg ccagcaaccc 720
ggaagtgatc gcccgcaccc tgcgtaaact gaaaaaccag ccggaactga gcgaagacac 780
catcaaaaaa gcagtggaat cgctgtcgct ggaactggtc ctcacggctc acccaaccga 840
aattacccgt cgtacactga tccacaaaat ggtggaagtg aacgcctgtt taaaacagct 900
cgataacaaa gatatcgctg actacgaaca caaccagctg atgcgtcgcc tgcgccagtt 960
gatcgcccag tcatggcata ccgatgaaat ccgtaagctg cgtccaagcc cggtagatga 1020
agccaaatgg ggctttgccg tagtggaaaa cagcctgtgg caaggcgtac caaattacct 1080
gcgcgaactg aacgaacaac tggaagagaa cctcggctac aaactgcccg tcgaatttgt 1140
tccggtccgt tttacttcgt ggatgggcgg cgaccgcgac ggcaacccga acgtcactgc 1200
cgatatcacc cgccacgtcc tgctactcag ccgctggaaa gccaccgatt tgttcctgaa 1260
agatattcag gtgctggttt ctgaactgtc gatggttgaa gcgacccctg aactgctggc 1320
gctggttggc gaagaaggtg ccgcagaacc gtatcgctat ctgatgaaaa acctgcgttc 1380
tcgcctgatg gcgacacagg catggctgga agcgcgcctg aaaggcgaag aactgccaaa 1440
accagaaggc ctgctgacac aaaacgaaga actgtgggaa ccgctctacg cttgctacca 1500
gtcacttcag gcgtgtggca tgggtattat cgccaacggc gatctgctcg acaccctgcg 1560
ccgcgtgaaa tgtttcggcg taccgctggt ccgtattgat atccgtcagg agagcacgcg 1620
tcataccgaa gcgctgggcg agctgacccg ctacctcggt atcggcgact acgaaagctg 1680
gtcagaggcc gacaaacagg cgttcctgat ccgcgaactg aactccaaac gtccgcttct 1740
gccgcgcaac tggcaaccaa gcgccgaaac gcgcgaagtg ctcgatacct gccaggtgat 1800
tgccgaagca ccgcaaggct ccattgccgc ctacgtgatc tcgatggcga aaacgccgtc 1860
cgacgtactg gctgtccacc tgctgctgaa agaagcgggt atcgggtttg cgatgccggt 1920
tgctccgctg tttgaaaccc tcgatgatct gaacaacgcc aacgatgtca tgacccagct 1980
gctcaatatt gactggtatc gtggcctgat tcagggcaaa cagatggtga tgattggcta 2040
ttccgactca gcaaaagatg cgggagtgat ggcagcttcc tgggcgcaat atcaggcaca 2100
ggatgcatta atcaaaacct gcgaaaaagc gggtattgag ctgacgttgt tccacggtcg 2160
cggcggttcc attggtcgcg gcggcgcacc tgctcatgcg gcgctgctgt cacaaccgcc 2220

-continued aggaagcctg aaaggcggcc tgcgcgtaac cgaacagggc gagatgatcc gctttaaata 2280
tggtctgcca gaaatcaccg tcagcagcct gtcgctttat accggggcga ttctggaagc 2340
caacctgctg ccaccgccgg agccgaaaga gagctggcgt cgcattatgg atgaactgtc 2400
agtcatctcc tgcgatgtct accgcggcta cgtacgtgaa aacaaagatt ttgtgcctta 2460
cttccgctcc gctacgccgg aacaagaact gggcaaactg ccgttgggtt cacgtccggc 2520
gaaacgtcgc ccaaccggcg gcgtcgagtc actacgcgcc attccgtgga tcttcgcctg 2580
gacgcaaaac cgtctgatgc tccccgcctg gctgggtgca ggtacggcgc tgcaaaaagt 2640
ggtcgaagac ggcaaacaga gcgagctgga ggctatgtgc cgcgattggc cattcttctc 2700
gacgcgtctc ggcatgctgg agatggtctt cgccaaagca gacctgtggc tggcggaata 2760
ctatgaccaa cgcctggtag acaaagcact gtggccgtta ggtaaagagt tacgcaacct 2820
gcaagaagaa gacatcaaag tggtgctggc gattgccaac gattcccatc tgatggccga 2880
tctgccgtgg attgcagagt ctattcagct acggaatatt tacaccgacc cgctgaacgt 2940
attgcaggcc gagttgctgc accgctcccg ccaggcagaa aaagaaggcc aggaaccgga 3000
tcctcgcgtc gaacaagcgt taatggtcac tattgccggg attgcggcag gtatgcgtaa 3060
taccggctaa tcttcctctt ctgcaaaccc tcgtgctttt gcgcgagggt tttctgaaat 3120
acttc 3125

<210> SEQ ID NO 15
<211> LENGTH: 1563
<212> TYPE: DNA
<213> ORGANISM: Escherichia coli W3110

<400> SEQUENCE: 15
gatccgtcca cctatgttga ctacatcatc aaccagatcg attctgacaa caaactgggc 60
gtaggttcag acgacaccgt tgctgtgggt atcgtttacc agttctaata gcacacctct 120
ttgttaaatg ccgaaaaaac aggactttgg tcctgttttt tttatacctt ccagagcaat 180
ctcacgtctt gcaaaaacag cctgcgtttt catcagtaat agttggaatt ttgtaaatct 240
cccgttaccc tgatagcgga cttcccttct gtaaccataa tggaacctcg tcatgtttga 300
gaacattacc gccgctcctg ccgacccgat tctgggcctg gccgatctgt ttcgtgccga 360
tgaacgtccc ggcaaaatta acctcgggat tggtgtctat aaagatgaga cgggcaaaac 420
cccggtactg accagcgtga aaaaggctga acagtatctg ctcgaaaatg aaaccaccaa 480
aaattacctc ggcattgacg gcatccctga atttggtcgc tgcactcagg aactgctgtt 540
tggtaaaggt agcgccctga tcaatgacaa acgtgctcgc acggcacaga ctccgggggg 600
cactggcgca ctacgcgtgg ctgccgattt cctggcaaaa aataccagcg ttaagcgtgt 660
gtgggtgagc aacccaagct ggccgaacca taagagcgtc tttaactctg caggtctgga 720
agttcgtgaa tacgcttatt atgatgcgga aaatcacact cttgacttcg atgcactgat 780
taacagcctg aatgaagctc aggctggcga cgtagtgctg ttccatggct gctgccataa 840
cccaaccggt atcgacccta cgctggaaca atggcaaaca ctggcacaac tctccgttga 900
gaaaggctgg ttaccgctgt ttgacttcgc ttaccagggt tttgcccgtg gtctggaaga 960
agatgctgaa ggactgcgcg ctttcgcggc tatgcataaa gagctgattg ttgccagttc 1020
ctactctaaa aactttggcc tgtacaacga gcgtgttggc gcttgtactc tggttgctgc 1080
cgacagtgaa accgttgatc gcgcattcag ccaaatgaaa gcggcgattc gcgctaacta 1140
ctctaaccca ccagcacacg gcgcttctgt tgttgccacc atcctgagca acgatgcgtt 1200

```
acgtgcgatt tgggaacaag agctgactga tatgcgccag cgtattcagc gtatgcgtca   1260

gttgttcgtc aatacgctgc aggaaaaagg cgcaaaccgc gacttcagct ttatcatcaa   1320

acagaacggc atgttctcct tcagtggcct gacaaaagaa caagtgctgc gtctgcgcga   1380

agagtttggc gtatatgcgg ttgcttctgg tcgcgtaaat gtggccggga tgacaccaga   1440

taacatggct ccgctgtgcg aagcgattgt ggcagtgctg taagcattaa aaacaatgaa   1500

gcccgctgaa aagcgggctg agactgatga caaacgcaac attgcctgat gcgctacgct   1560

tat                                                                 1563
```

<210> SEQ ID NO 16
<211> LENGTH: 1556
<212> TYPE: DNA
<213> ORGANISM: Escherichia coli W3110

<400> SEQUENCE: 16

```
gaattcccag gagagcaata agcaactctc gcaccatgat tgcccgccgt cttttcggtt     60

cagtatgttt cagtacggac atgaaaatag gtaggtttcc gagcggatcc ataatcagga    120

tcaataaaac tgctgcagaa atgatttcat tcataactca aattccctga taattgccgc    180

ggactttctg cgtgctaaca aagcaggata agtcgcatta ctgatggctt cgctatcatt    240

gattaatttc acttgcgact ttggctgctt tttgtatggt gaaagatgtg ccaagaggag    300

accggcacat ttatacagca cacatctttg caggaaaaaa acgcttatga aaaatgttgg    360

ttttatcggc tggcgcggta tggtcggctc cgttctcatg caacgcatgg ttgaagagcg    420

cgacttcgac gccattcgcc ctgtcttctt ttctacttct cagcttggcc aggctgcgcc    480

gtcttttggc ggaaccactg gcacacttca ggatgccttt gatctggagg cgctaaaggc    540

cctcgatatc attgtgacct gtcagggcgg cgattatacc aacgaaatct atccaaagct    600

tcgtgaaagc ggatggcaag gttactggat tgacgcagca tcgtctctgc gcatgaaaga    660

tgacgccatc atcattcttg accccgtcaa tcaggacgtc attaccgacg gattaaataa    720

tggcatcagg acttttgttg gcggtaactg taccgtaagc ctgatgttga tgtcgttggg    780

tggtttattc gccaatgatc ttgttgattg ggtgtccgtt gcaacctacc aggccgcttc    840

cggcggtggt gcgcgacata tgcgtgagtt attaacccag atgggccatc tgtatggcca    900

tgtggcagat gaactcgcga ccccgtcctc tgctattctc gatatcgaac gcaaagtcac    960

aaccttaacc cgtagcggtg agctgccggt ggataacttt ggcgtgccgc tggcgggtag   1020

cctgattccg tggatcgaca aacagctcga taacggtcag agccgcgaag agtggaaagg   1080

gcaggcggaa accaacaaga tcctcaacac atcttccgta attccggtag atggtttatg   1140

tgtgcgtgtc ggggcattgc gctgccacag ccaggcattc actattaaat tgaaaaaaga   1200

tgtgtctatt ccgaccgtgg aagaactgct ggctgcgcac aatccgtggg cgaaagtcgt   1260

tccgaacgat cgggaaatca ctatgcgtga gctaacccca gctgccgtta ccggcacgct   1320

gaccacgccg gtaggccgcc tgcgtaagct gaatatggga ccagagttcc tgtcagcctt   1380

taccgtgggc gaccagctgc tgtggggggc cgcggagccg ctgcgtcgga tgcttcgtca   1440

actggcgtaa tctttattca ttaaatctgg ggcgcgatgc cgcccctgtt agtgcgtaat   1500

acaggagtaa gcgcagatgt ttcatgattt accgggagtt aaatagagca tctaga       1556
```

<210> SEQ ID NO 17
<211> LENGTH: 2464
<212> TYPE: DNA
<213> ORGANISM: Escherichia coli W3110

-continued

<400> SEQUENCE: 17

```
atgcgagtgt tgaagttcgg cggtacatca gtggcaaatg cagaacgttt tctgcgtgtt     60
gccgatattc tggaaagcaa tgccaggcag gggcaggtgg ccaccgtcct ctctgccccc    120
gccaaaatca ccaaccacct ggtggcgatg attgaaaaaa ccattagcgg ccaggatgct    180
ttacccaata tcagcgatgc cgaacgtatt tttgccgaac ttttgacggg actcgccgcc    240
gcccagccgg ggttcccgct ggcgcaattg aaaactttcg tcgatcagga atttgcccaa    300
ataaaacatg tcctgcatgg cattagtttg ttggggcagt gcccggatag catcaacgct    360
gcgctgattt gccgtggcga gaaaatgtcg atcgccatta tggccggcgt attagaagcg    420
cgcggtcaca acgttactgt tatcgatccg gtcgaaaaac tgctggcagt ggggcattac    480
ctcgaatcta ccgtcgatat tgctgagtcc acccgccgta ttgcggcaag ccgcattccg    540
gctgatcaca tggtgctgat ggcaggtttc accgccggta atgaaaaagg cgaactggtg    600
gtgcttggac gcaacggttc cgactactct gctgcggtgc tggctgcctg tttacgcgcc    660
gattgttgcg agatttggac ggacgttgac ggggtctata cctgcgaccc gcgtcaggtg    720
cccgatgcga ggttgttgaa gtcgatgtcc taccaggaag cgatggagct ttcctacttc    780
ggcgctaaag ttcttcaccc ccgcaccatt acccccatcg cccagttcca gatcccttgc    840
ctgattaaaa ataccggaaa tcctcaagca ccaggtacgc tcattggtgc cagccgtgat    900
gaagacgaat taccggtcaa gggcatttcc aatctgaata acatggcaat gttcagcgtt    960
tctggtccgg ggatgaaagg gatggtcggc atggcggcgc gcgtctttgc agcgatgtca   1020
cgcgcccgta tttccgtggt gctgattacg caatcatctt ccgaatacag catcagtttc   1080
tgcgttccac aaagcgactg tgtgcgagct gaacgggcaa tgcaggaaga gttctacctg   1140
gaactgaaag aaggcttact ggagccgctg gcagtgacgg aacggctggc cattatctcg   1200
gtggtaggtg atggtatgcg caccttgcgt gggatctcgg cgaaattctt tgccgcactg   1260
gcccgcgcca atatcaacat tgtcgccatt gctcagggat cttctgaacg ctcaatctct   1320
gtcgtggtaa ataacgatga tgcgaccact ggcgtgcgcg ttactcatca gatgctgttc   1380
aataccgatc aggttatcga agtgtttgtg attggcgtcg gtggcgttgg cggtgcgctg   1440
ctggagcaac tgaagcgtca gcaaagctgg ctgaagaata aacatatcga cttacgtgtc   1500
tgcggtgttg ccaactcgaa ggctctgctc accaatgtac atggccttaa tctggaaaac   1560
tggcaggaag aactggcgca agccaaagag ccgtttaatc tcgggcgctt aattcgcctc   1620
gtgaaagaat atcatctgct gaacccggtc attgttgact gcacttccag ccaggcagtg   1680
gcggatcaat atgccgactt cctgcgcgaa ggtttccacg ttgtcacgcc gaacaaaaag   1740
gccaacacct cgtcgatgga ttactaccat cagttgcgtt atgcggcgga aaaatcgcgg   1800
cgtaaattcc tctatgacac caacgttggg gctggattac cggttattga gaacctgcaa   1860
aatctgctca atgcaggtga tgaattgatg aagttctccg gcattctttc tggttcgctt   1920
tcttatatct tcggcaagtt agacgaaggc atgagtttct ccgaggcgac cacgctggcg   1980
cgggaaatgg gttataccga accggacccg cgagatgatc tttctggtat ggatgtggcg   2040
cgtaaactat tgattctcgc tcgtgaaacg ggacgtgaac tggagctggc ggatattgaa   2100
attgaacctg tgctgcccgc agagtttaac gccgagggtg atgttgccgc ttttatggcg   2160
aatctgtcac aactcgacga tctctttgcc gcgcgcgtgg cgaaggcccg tgatgaagga   2220
aaagttttgc gctatgttgg caatattgat gaagatggcg tctgccgcgt gaagattgcc   2280
gaagtggatg gtaatgatcc gctgttcaaa gtgaaaaatg gcgaaaacgc cctggccttc   2340
```

-continued tatagccact attatcagcc gctgccgttg gtactgcgcg gatatggtgc gggcaatgac 2400
gttacagctg ccggtgtctt tgctgatctg ctacgtaccc tctcatggaa gttaggagtc 2460
tgaa 2464

<210> SEQ ID NO 18
<211> LENGTH: 334
<212> TYPE: PRT
<213> ORGANISM: Deinococcus radiodurans

<400> SEQUENCE: 18

Met Thr Ala Val Leu Ala Gly His Ala Ser Ala Leu Leu Leu Thr Glu
1 5 10 15

Glu Pro Asp Cys Ser Gly Pro Gln Thr Val Val Leu Phe Arg Arg Glu
20 25 30

Pro Leu Leu Leu Asp Cys Gly Arg Ala Leu Ser Asp Val Arg Val Ala
35 40 45

Phe His Thr Tyr Gly Thr Pro Arg Ala Asp Ala Thr Leu Val Leu His
50 55 60

Ala Leu Thr Gly Asp Ser Ala Val His Glu Trp Trp Pro Asp Phe Leu
65 70 75 80

Gly Ala Gly Arg Pro Leu Asp Pro Ala Asp Asp Tyr Val Val Cys Ala
85 90 95

Asn Val Leu Gly Gly Cys Ala Gly Thr Thr Ser Ala Ala Glu Leu Ala
100 105 110

Ala Thr Cys Ser Gly Pro Val Pro Leu Ser Leu Arg Asp Met Ala Arg
115 120 125

Val Gly Arg Ala Leu Leu Asp Ser Leu Gly Val Arg Arg Val Arg Val
130 135 140

Ile Gly Ala Ser Met Gly Gly Met Leu Ala Tyr Ala Trp Leu Leu Glu
145 150 155 160

Cys Pro Asp Leu Val Glu Lys Ala Val Ile Ile Gly Ala Pro Ala Arg
165 170 175

His Ser Pro Trp Ala Ile Gly Leu Asn Thr Ala Ala Arg Ser Ala Ile
180 185 190

Ala Leu Ala Pro Gly Gly Glu Gly Leu Lys Val Ala Arg Gln Ile Ala
195 200 205

Met Leu Ser Tyr Arg Ser Pro Glu Ser Leu Ser Arg Thr Gln Ala Gly
210 215 220

Gln Arg Val Pro Gly Val Pro Ala Val Thr Ser Tyr Leu His Tyr Gln
225 230 235 240

Gly Glu Lys Leu Ala Ala Arg Phe Asp Glu Gln Thr Tyr Cys Ala Leu
245 250 255

Thr Trp Ala Met Asp Ala Phe Gln Pro Ser Ser Ala Asp Leu Lys Ala
260 265 270

Val Arg Ala Pro Val Leu Val Val Gly Ile Ser Ser Asp Leu Leu Tyr
275 280 285

Pro Ala Ala Glu Val Arg Ala Cys Ala Ala Glu Leu Pro His Ala Asp
290 295 300

Tyr Trp Glu Leu Gly Ser Ile His Gly His Asp Ala Phe Leu Met Asp
305 310 315 320

Pro Gln Asp Leu Pro Glu Arg Val Gly Ala Phe Leu Arg Ser
325 330

<210> SEQ ID NO 19
<211> LENGTH: 379

-continued

<212> TYPE: PRT
<213> ORGANISM: Pseudomonas aeruginosa PAO1

<400> SEQUENCE: 19

```
Met Pro Thr Val Phe Pro Asp Asp Ser Val Gly Leu Val Ser Pro Gln
 1               5                  10                  15

Thr Leu His Phe Asn Glu Pro Leu Glu Leu Thr Ser Gly Lys Ser Leu
            20                  25                  30

Ala Glu Tyr Asp Leu Val Ile Glu Thr Tyr Gly Glu Leu Asn Ala Thr
        35                  40                  45

Gln Ser Asn Ala Val Leu Ile Cys His Ala Leu Ser Gly His His His
    50                  55                  60

Ala Ala Gly Tyr His Ser Val Asp Glu Arg Lys Pro Gly Trp Trp Asp
65                  70                  75                  80

Ser Cys Ile Gly Pro Gly Lys Pro Ile Asp Thr Arg Lys Phe Phe Val
                85                  90                  95

Val Ala Leu Asn Asn Leu Gly Gly Cys Asn Gly Ser Ser Gly Pro Ala
            100                 105                 110

Ser Ile Asn Pro Ala Thr Gly Lys Val Tyr Gly Ala Asp Phe Pro Met
        115                 120                 125

Val Thr Val Glu Asp Trp Val His Ser Gln Ala Arg Leu Ala Asp Arg
    130                 135                 140

Leu Gly Ile Arg Gln Trp Ala Ala Val Val Gly Gly Ser Leu Gly Gly
145                 150                 155                 160

Met Gln Ala Leu Gln Trp Thr Ile Ser Tyr Pro Glu Arg Val Arg His
                165                 170                 175

Cys Leu Cys Ile Ala Ser Ala Pro Lys Leu Ser Ala Gln Asn Ile Ala
            180                 185                 190

Phe Asn Glu Val Ala Arg Gln Ala Ile Leu Ser Asp Pro Glu Phe Leu
        195                 200                 205

Gly Gly Tyr Phe Gln Glu Gln Gly Val Ile Pro Lys Arg Gly Leu Lys
    210                 215                 220

Leu Ala Arg Met Val Gly His Ile Thr Tyr Leu Ser Asp Asp Ala Met
225                 230                 235                 240

Gly Ala Lys Phe Gly Arg Val Leu Lys Thr Glu Lys Leu Asn Tyr Asp
                245                 250                 255

Leu His Ser Val Glu Phe Gln Val Glu Ser Tyr Leu Arg Tyr Gln Gly
            260                 265                 270

Glu Glu Phe Ser Thr Arg Phe Asp Ala Asn Thr Tyr Leu Leu Met Thr
        275                 280                 285

Lys Ala Leu Asp Tyr Phe Asp Pro Ala Ala Ala His Gly Asp Asp Leu
    290                 295                 300

Val Arg Thr Leu Glu Gly Val Glu Ala Asp Phe Cys Leu Met Ser Phe
305                 310                 315                 320

Thr Thr Asp Trp Arg Phe Ser Pro Ala Arg Ser Arg Glu Ile Val Asp
                325                 330                 335

Ala Leu Ile Ala Ala Lys Lys Asn Val Ser Tyr Leu Glu Ile Asp Ala
            340                 345                 350

Pro Gln Gly His Asp Ala Phe Leu Met Pro Ile Pro Arg Tyr Leu Gln
        355                 360                 365

Ala Phe Ser Gly Tyr Met Asn Arg Ile Ser Val
    370                 375
```

<210> SEQ ID NO 20
<211> LENGTH: 380

-continued

<212> TYPE: PRT
<213> ORGANISM: Mycobacterium smegmatis str. MC2 155

<400> SEQUENCE: 20

```
Met Thr Ile Ile Glu Glu Arg Ala Thr Asp Thr Gly Met Ala Thr Val
 1               5                  10                  15

Pro Leu Pro Ala Glu Gly Glu Ile Gly Leu Val His Ile Gly Ala Leu
            20                  25                  30

Thr Leu Glu Asn Gly Thr Val Leu Pro Asp Val Thr Ile Ala Val Gln
        35                  40                  45

Arg Trp Gly Glu Leu Ala Pro Asp Arg Gly Asn Val Val Met Val Leu
    50                  55                  60

His Ala Leu Thr Gly Asp Ser His Val Thr Gly Pro Ala Gly Asp Gly
65                  70                  75                  80

His Pro Thr Ala Gly Trp Trp Asp Gly Val Ala Gly Pro Gly Ala Pro
                85                  90                  95

Ile Asp Thr Asp His Trp Cys Ala Ile Ala Thr Asn Val Leu Gly Gly
            100                 105                 110

Cys Arg Gly Ser Thr Gly Pro Gly Ser Leu Ala Pro Asp Gly Lys Pro
        115                 120                 125

Trp Gly Ser Arg Phe Pro Gln Ile Thr Ile Arg Asp Gln Val Ala Ala
    130                 135                 140

Asp Arg Ala Ala Leu Ala Ala Leu Gly Ile Thr Glu Val Ala Ala Val
145                 150                 155                 160

Val Gly Gly Ser Met Gly Gly Ala Arg Ala Leu Glu Trp Leu Val Thr
                165                 170                 175

His Pro Asp Asp Val Arg Ala Gly Leu Val Leu Ala Val Gly Ala Arg
            180                 185                 190

Ala Thr Ala Asp Gln Ile Gly Thr Gln Ser Thr Gln Val Ala Ala Ile
        195                 200                 205

Lys Ala Asp Pro Asp Trp Gln Gly Gly Asp Tyr His Gly Thr Gly Arg
    210                 215                 220

Ala Pro Thr Glu Gly Met Glu Ile Ala Arg Arg Phe Ala His Leu Thr
225                 230                 235                 240

Tyr Arg Gly Glu Glu Glu Leu Asp Asp Arg Phe Ala Asn Thr Pro Gln
                245                 250                 255

Asp Asp Glu Asp Pro Leu Thr Gly Gly Arg Tyr Ala Val Gln Ser Tyr
            260                 265                 270

Leu Glu Tyr Gln Gly Gly Lys Leu Ala Arg Arg Phe Asp Pro Gly Thr
        275                 280                 285

Tyr Val Val Leu Ser Asp Ala Leu Ser Ser His Asp Val Gly Arg Gly
    290                 295                 300

Arg Gly Gly Val Glu Ala Ala Leu Arg Ser Cys Pro Val Pro Val Val
305                 310                 315                 320

Val Gly Gly Ile Thr Ser Asp Arg Leu Tyr Pro Ile Arg Leu Gln Gln
                325                 330                 335

Glu Leu Ala Glu Leu Leu Pro Gly Cys Gln Gly Leu Asp Val Val Asp
            340                 345                 350

Ser Ile Tyr Gly His Asp Gly Phe Leu Val Glu Thr Glu Leu Val Gly
        355                 360                 365

Lys Leu Ile Arg Arg Thr Leu Glu Leu Ala Gln Arg
    370                 375                 380
```